United States Patent [19]

Shigematsu et al.

[11] 4,088,767
[45] May 9, 1978

[54] 4-DICHLOROPHENYLURAZOLE COMPOUNDS AND USE IN AGRICULTURAL FUNGICIDAL COMPOSITIONS

[75] Inventors: Taichiro Shigematsu; Tetsuya Shibahara; Makoto Nakazawa, all of Yokohama; Masayuki Tomida, Sagamihara; Toshio Munakata, Tokyo, all of Japan

[73] Assignee: Mitsubishi Chemical Industries Limited, Tokyo, Japan

[21] Appl. No.: 637,740

[22] Filed: Dec. 4, 1975

[30] Foreign Application Priority Data

Dec. 6, 1974 Japan .................................. 49-140224

[51] Int. Cl.² .......................... A01N 9/12; A01N 9/22; A01N 21/00; C07D 249/12

[52] U.S. Cl. ................ 424/269; 260/308 C; 424/168; 424/170; 424/171; 560/9; 560/34; 560/169

[58] Field of Search ..................... 260/308 C; 424/269

[56] References Cited

U.S. PATENT DOCUMENTS

| 3,184,470 | 5/1965 | Ruschig et al. .................. 260/308 C |
| 3,663,564 | 5/1972 | Jacobson et al. ................ 260/308 C |
| 3,912,735 | 10/1975 | Von Bredow et al. ......... 260/308 C |

*Primary Examiner*—Alton D. Rollins
*Attorney, Agent, or Firm*—Bierman & Bierman

[57] ABSTRACT

There is disclosed a fungicide comprising as active ingredient a 1,2-substituted-4-(3′,5′-dichlorophenyl) urazole derivative suitable for preventing various diseases of plants including fruit trees, vegetables, rice plants and beans.

10 Claims, No Drawings

4-DICHLOROPHENYLURAZOLE COMPOUNDS AND USE IN AGRICULTURAL FUNGICIDAL COMPOSITIONS

This application claims the benefit of the priority of Japanese application No. 140224/74 filed Dec. 6, 1975.

This invention relates to an agricultural fungicide. A wide variety of agricultural fungicides have been developed, but some of them are not used because they cause ecological pollution. We have conducted intensive studies to find an agricultural fungicide which posses superior fungicidal effects coupled with low toxicity and have found that certain urazole derivatives have these desirable properties.

Accordingly, this invention provides a novel agricultural fungicide which comprises, as the active ingredient, a 1,2-substituted-4-(3′,5′-dichlorophenyl) urazole represented by the general formula:

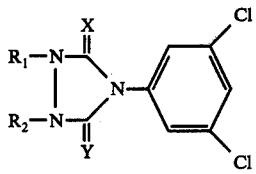

wherein $R_1$ and $R_2$ may be the same or different and represent alkyl, alkenyl, alkynyl, and/or aryl (which may have at least one substituent selected from the group consisting of halogen and alkyl), acyl, alkylcarbamoyl, alkoxycarbonyl, alkylthiocarbamoyl and/or (alkylthio) thiocarbamoyl; and X and Y may be the same or different and are oxygen and/or sulfur.

It has already been found that some 1,2,4-substituted urazole derivatives have fungicidal, herbicidal and insecticidal activities. Compounds represented by the above general formula are novel and possess excellent fungicidal activity against a wide variety of plant diseases but are nonpathogenic to the host plant and have no or little toxicity to humans and fish.

The fungicides according to this invention are especially effective against rice sheath blight disease, Botrytis gray mold disease, rice brown spot disease, Sclerotinia rot and Alternaria leaf spot and, in some cases, two or more diseases are prevented simultaneously.

The compounds which are suitable for this invention are prepared through various routes.

Route A

A salt of 4-(3′,5′-dichlorophenyl) urazole is reacted with an alkyl halide in a solvent, such as dimethylformamide, alcohol or acetone at from room to an elevated temperature for a few hours to produce the desired product in accordance with the following reaction:

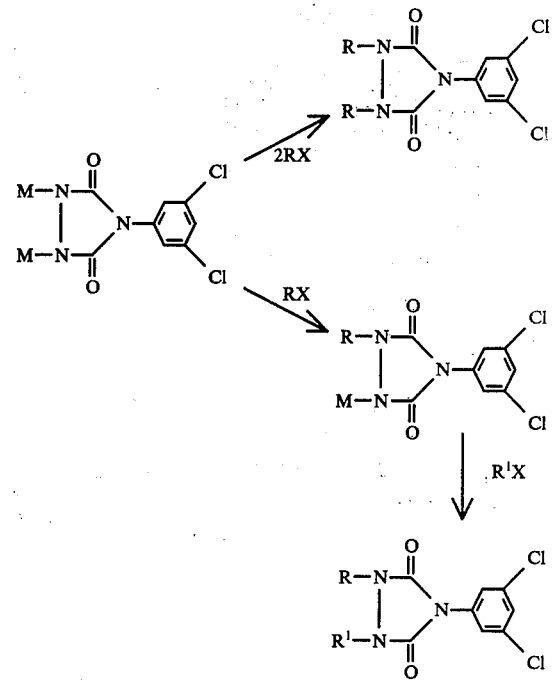

wherein R and $R^1$ may be the same or different and represent alkyl, alkenyl, alkynyl, acyl, alkoxycarbonyl and/or alkoxythiocarbonyl, and M represents alkali metal, alkaline earth metal or $NH_4$-, and X represents a halogen.

By varying the molar proportions of the reactants and type of alkyl halide, monosubstituted and disubstituted derivatives and disubstituted derivatives containing different substituents are prepared.

Route B

In the presence of a solvent, such as dimethylformamide, acetone or tetrahydrofuran, 4-(3,5-dichlorophenyl) urazole is reacted with an isocyanate or a thioisocyanate in the presence of a basic catalyst such as triethylamine and pyridine at from room to an elevated temperature for a several hours to prepare 1-mono- or 1,2-di-alkylcarbamoyl (or alkylthiocarbamoyl) derivatives in accordance with the following equations:

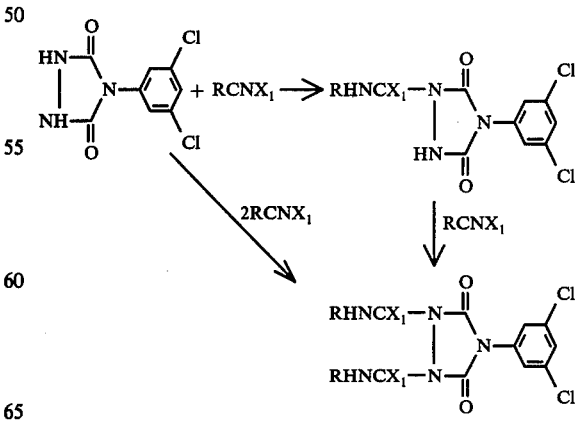

wherein R represents alkyl and $X_1$ represents oxygen or sulfur.

As in Route A, mono- or di-substituted derivatives are selectively prepared by varying the proportions of the reactants.

Route C

A solution of 1,2-substituted-4-(3',5'-dichlorophenyl) urazole in a solvent, such as xylene or cumene is treated with two molar equivalents of phosphorus pentasulfide under reflux for a few hours to produce the di-thio derivative.

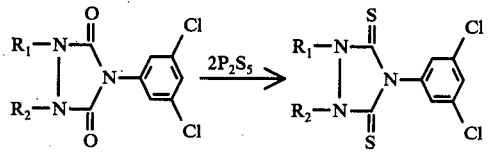

wherein $R_1$ and $R_2$ have the same meanings as above.

Route D

To a solution of 1,2-substituted-1-alkoxycarbonyl hydrazine in a solvent such as benzene, toluene or xylene is added in small increments 3,5-dichlorophenylisocyanate in a stoichiometric amount to form 1,2-substituted-1-alkoxycarbonyl-2-(3',5'-dichlorophenyl) hydrazine which is precipitated by distilling off the solvent, filtered off and dried. It is then dissolved in an aqueous solution of potassium hydroxide or sodium alcoholate with agitation and heating, followed by cooling and the addition of an acid to precipitate 1,2-substituted-4-(3',5'-dichlorophenyl) urazole as shown below:

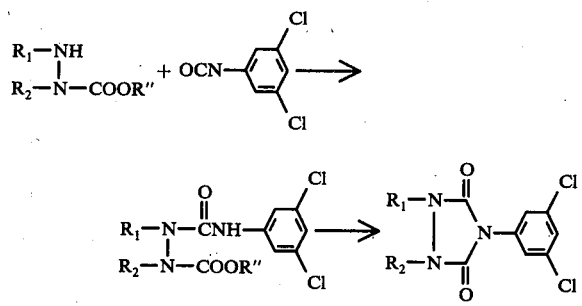

wherein $R_1$ and $R_2$ have the same meanings as above and R" represents lower alkyl.

Route E

To a solution of 1,2-substituted-1-alkoxycarbonyl hydrazine in a solvent such as benzene, toluene, xylene or cumene is added a stoichiometric amount of dropwise 3,5-dichlorophenyl isothiocyanate to produce 1,2-substituted 1-alkoxycarbonyl-2-(3',5'-dichlorophenyl thiocarbamoyl) hydrazine, and the resulting reaction mixture is refluxed for from a few to 10-odd hours to obtain a desired monothiourazole product as follows:

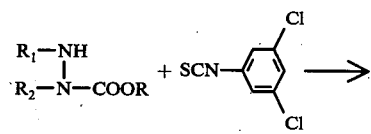

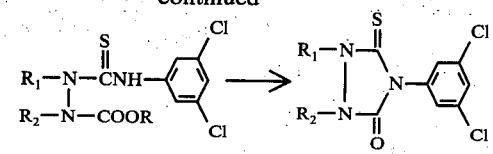

wherein $R_1$ and $R_2$ have the same meanings as above.

The preparation of the compound which may be used as active ingredient according to this invention will be explained in detail by means of the following Reference Examples.

REFERENCE EXAMPLE 1

To a suspension of the 3.2 g of dipotassium salt of 4-(3',5'-dichlorophenyl) urazole in 20 ml of dried, N,N-dimethylformamide was added 2.9 g of methyl iodide, and the reaction mixture was heated to and held at a temperature of 60 to 70° C for one hour with agitation. After removing the N,N-dimethylformamide by distillation in vacuo, the resultant mass was poured into 200 ml of water to precipitate the solid material which was then recrystallized from ethanol to obtain 2.6 g of 1,2-dimethyl-4-(3',5'-dichlorophenyl) urazole, the yield being 95%.

The melting point and elementary analysis of the product are given in Table 1.

REFERENCE EXAMPLE 2

To a solution of 2.5 g of 4-(3',5'-dichlorophenyl) urazole and 1 g of triethylamine in 10 ml of N,N-dimethylformamide was added dropwise 1.1 g of ethylchloroformate with agitation. The reaction and agitation were continued at room temperature for one hour. The reaction mass was mixed with water to precipitate crystals which were filtered and recrystallized from acetone-ethanol to obtain 2.3 g of 1-ethoxycarbonyl-4-(3',5'-dichlorophenyl) urazole, which constituted a yield of 72%.

REFERENCE EXAMPLE 3

To a solution of 2.6 g of 1-methyl-4-(3',5'-dichlorophenyl) urazole, which had been prepared by reacting 4-(3',5'-dichlorophenyl) urazole and methyl bromide in an equimolar proportion, and 1.0 g of triethylamine in 10 ml of N,N-dimethylformamide was added 0.8 g of acetyl chloride in small increments at room temperature with agitation. After completing the addition, the reaction was carried out on a water bath for 2 hours with continued agitation. The solvent was removed by distillation into vacuo and the mass was poured in water to precipitate crystals which were recrystallized from ethanol to obtain 2.3 g of 1-methyl-2-acetyl-4-(3',5'-dichlorophenyl) urazole in a yield of 76%.

REFERENCE EXAMPLE 4

To a solution of 2.5 g of 4-(3',5'-dichlorophenyl) urazole in 10 ml of N,N-dimethylformamide were added a drop of triethylamine and, in turn, 0.8 g of methyl isocyanate dropwise at room temperature with agitation. The reaction was continued for one additional hour under the same conditions and the reaction mixture was poured in water to precipitate crystals which were filtered and recrystallized from acetoneethanol to obtain 1-methylcarbamoyl-4-(3',5'-dichlorophenyl) urazole in an amount of 2.1 g (yield being 68%).

REFERENCE EXAMPLE 5

A solution of 2.7 g of 1,2-dimethyl-4-(3',5'-dichlorophenyl) urazole in 25 ml of xylene and 4.4 g of phosphorus pentasulfide were mixed and heated under reflux for 8 hours with agitation. After cooling and filtration, the filtrate was concentrated in vacuo. The residue was recrystallized from ethanol to obtain 1.4 g of 1,2-dimethyl-4-(3',5'-dichlorophenyl) dithiourazole (the yield being 47%).

REFERENCE EXAMPLE 6

To a solution of 1.6 g of 1,2-dimethyl-ethoxycarbonyl hydrazine in 25 ml of benzene was added 1.9 g of 2,5-dichlorophenyl isocyanate in small increments at room temperature with agitation. By removing benzene in vacuo, there were obtained crystals of 1,2-dimethyl-1-ethoxycarbonyl-2-(3',5'-dichlorophenyl carbamoyl) hydrazine having a melting point of 161° – 163° C. The elementary assay as $C_{12}H_{15}N_2O_3Cl_2$ was:

|  | C(%) | H(%) | N(%) | Cl(%) |
|---|---|---|---|---|
| Calculation | 45.01 | 4.72 | 13.12 | 22.15 |
| Found | 45.12 | 4.78 | 13.21 | 22.03 |

Then, the resulting product was reacted with sodium methoxide in equimolar amount in methanol under reflux for 6 hours and, after cooling, water was added to the reaction mixture to precipitate crystals which was filtered and recrystallized from ethanol to obtain 1,2-dimethyl-4-(3',5'-dichlorophenyl) urazole in an amount of 1.0 g (the yield being 37%).

The melting point was 209° – 211° C and the elementary assay as $C_{10}H_9N_3O_2Cl_2$ was:

|  | C(%) | H(%) | N(%) | Cl(%) |
|---|---|---|---|---|
| Calculation | 43.82 | 3.31 | 15.33 | 25.87 |
| Found | 43.49 | 3.30 | 15.42 | 25.81 |

REFERENCE EXAMPLE 7

Procedures similar to those of Reference Example 6 were repeated using 3,5-dichlorophenyl isothiocyanate to obtain 1,2-dimethyl-1-ethoxycarbonyl-2-(3',5'-dichlorophenyl thiocarbamoyl) hydrazine.

The melting point was 147° – 149° C and the elementary assay as $C_{12}H_{15}Cl_2N_2SO_2$ was:

|  | C(%) | H(%) | N(%) | Cl(%) | S(%) |
|---|---|---|---|---|---|
| Calculation | 42.86 | 4.50 | 12.50 | 21.09 | 9.54 |
| Found | 42.91 | 4.47 | 12.42 | 21.13 | 9.59 |

The compound was subjected to heat treatment in cumene under reflux for 10 hours to obtain 1.8 g of 1,2-dimethyl-4-(3',5'-dichlorophenyl) monothiourazole (the yield being 64%).

REFERENCE EXAMPLE 8

To a solution of 3.2 g of 1-ethoxycarbonyl-4-(3',5'-dichlorophenyl) urazole in 10 ml of N,N-dimethylformamide were added, in sequence, a drop of triethylamine and 0.85 g of isopropyl isocyanate dropwise at room temperature with agitation. After maintaining the same conditions for one hour, the reaction mixture was mixed with water to precipitate crystals which were filtered and recrystallized from ethanol to obtain 1-ethoxycarbonyl-2-(isopropyl carbamoyl)-4-(3',5'-dichlorophenyl) urazole in an amount of 3.0 g, a yield of 75%.

REFERENCE EXAMPLE 9

To a solution of 10.8 g of phenyl hydrazine and 10.1 g of triethylamine in 60 ml of benzene was added dropwise a solution of 10.9 g of ethyl chloroformate in 40 ml of benzene over 20 minutes while the mixture was maintained at a temperature of from 10° to 15° C with agitation.

The reaction was continued at room temperature for one hour with agitation. After adding water under agitation, the reaction mixture was allowed to stand until there was phase separation. The aqueous phase containing the triethylamine hydrochloric acid salt which was formed in the course of the reaction was removed. The organic phase was dried with anhydrous sodium sulfate. At room temperature, 18.8 g of 3,5-dichlorophenyl isocyanate was added dropwise to the benzene solution, then the mixture was heated on a water-bath to carry out the reaction.

The benzene was removed by distillation in vacuo to obtain an oily product which was mixed with 200 ml of a 5% aqueous potassium hydroxide and heated under reflux for about 2 hours. After cooling and filtration, the filtrate was mixed with concentrated hydrochloric acid to precipitate crystals which were filtered and recrystallized from ethanol to obtain 1-phenyl-4-(3',5'-dichlorophenyl) urazole in an amount of 23.2 g, a yield of 72%.

The melting point was above 250° C and the elementary assay as $C_{14}H_9N_3O_2Cl_2$ was:

|  | C(%) | H(%) | N(%) | Cl(%) |
|---|---|---|---|---|
| Calculation | 52.19 | 2.82 | 13.04 | 22.01 |
| Found | 52.42 | 2.87 | 12.95 | 21.88 |

A mixture of 3.2 g of the product thus produced, 20 ml of N,N-dimethylformamide, and 0.6 g of potassium hydroxide in 5 ml of water was agitated at room temperature for 30 minutes to give a potassium salt, then 1.4 g of methyl iodide was added thereto and agitation was continued at room temperature for one hour. After completion of the reaction, water was added to the mixture to precipitate crystals which were separated and recrystallized from ethanol to obtain 1-phenyl-2-methyl-4-(3',5'-dichlorophenyl) urazole.

Table 1

| Compd. No. | Structure | Melting point(° C) | Elementary assay (%)[2] | | | | | Ref.[3] Ex. |
|---|---|---|---|---|---|---|---|---|
| | | | C | H | N | Cl | S | |
| 1 | 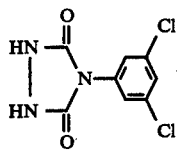 (1) | 275–276.5 | 39.05 | 2.05 | 17.08 | 28.82 | | 6 |
| | | | 38.95 | 2.02 | 17.21 | 28.85 | | |

Table 1-continued

| Compd. No. | Structure | Melting point (°C) | Elementary assay (%)[2] | | | | | Ref.[3] Ex. |
|---|---|---|---|---|---|---|---|---|
| | | | C | H | N | Cl | S | |
| 2 | CH₃N–CO–N(3,5-diClC₆H₃)–CO–NH | 189–192 | 41.56<br>41.46 | 2.71<br>2.68 | 16.16<br>16.22 | 27.26<br>27.31 | | 6 |
| 3 | CH₃N–CO–N(3,5-diClC₆H₃)–CO–NCH₃ | 209–211 | 43.82<br>43.57 | 3.31<br>3.29 | 15.33<br>15.19 | 25.87<br>26.02 | | 1 |
| 4 | CH₃N–CO–N(3,5-diClC₆H₃)–CO–NC₂H₅ | 115–117 | 45.85<br>45.83 | 3.85<br>3.81 | 14.58<br>14.47 | 24.61<br>24.55 | | 1 |
| 5 | CH₃N–CO–N(3,5-diClC₆H₃)–CO–N(nC₃H₇) | 90–91 | 47.70<br>47.54 | 4.34<br>4.31 | 13.91<br>13.87 | 23.47<br>23.52 | | 1 |
| 6 | CH₃N–CO–N(3,5-diClC₆H₃)–CO–N(i-C₃H₇) | 83–85 | 47.70<br>47.81 | 4.34<br>4.30 | 13.91<br>13.87 | 23.47<br>23.41 | | 1 |
| 7 | CH₃N–CO–N(3,5-diClC₆H₃)–CO–N(i-C₄H₉) | 92–92.5 | 49.38<br>49.27 | 4.78<br>4.69 | 13.29<br>13.27 | 22.43<br>22.14 | | 1 |
| 8 | C₂H₅N–CO–N(3,5-diClC₆H₃)–CO–NC₂H₅ | 109–111 | 47.70<br>47.53 | 4.34<br>4.22 | 13.91<br>13.99 | 23.47<br>23.56 | | 1 |
| 9 | n-C₃H₇N–CO–N(3,5-diClC₆H₃)–CO–N(n-C₃H₇) | 91–94 | 50.92<br>51.21 | 5.19<br>5.20 | 12.73<br>12.69 | 21.47<br>21.57 | | 1 |
| 10 | nC₄H₉N–CO–N(3,5-diClC₆H₃)–CO–N(nC₄H₉) | $n_D^{30}$ 1.5365 | 53.64<br>53.58 | 5.90<br>5.79 | 11.73<br>11.73 | 19.79<br>19.67 | | 1 |
| 11 | i-C₃H₇N–CO–N(3,5-diClC₆H₃)–CO–NH | 142–146 | 45.85<br>45.90 | 3.85<br>3.81 | 14.58<br>14.55 | 24.61<br>24.68 | | 1 |
| 12 | i-C₄H₉N–CO–N(3,5-diClC₆H₃)–CO–NH | 133–135 | 47.70<br>47.35 | 4.34<br>4.34 | 13.91<br>13.87 | 23.47<br>23.51 | | 1 |

Table 1-continued

| Compd. No. | Structure | Melting point (°C) | Elementary assay (%)[2] | | | | | Ref.[3] Ex. |
|---|---|---|---|---|---|---|---|---|
| | | | C | H | N | Cl | S | |
| 13 | CH₃CON-, HN-, 3,5-diCl-C₆H₃ | 226–228 | 41.69<br>41.65 | 2.45<br>2.43 | 14.59<br>14.58 | 24.61<br>24.60 | | 3 |
| 14 | C₂H₅CON-, HN-, 3,5-diCl-C₆H₃ | 193–194 | 43.73<br>43.68 | 3.00<br>3.02 | 13.90<br>13.88 | 23.47<br>23.54 | | 3 |
| 15 | CH₃CON-, CH₃CON-, 3,5-diCl-C₆H₃ | 226–227 | 43.66<br>43.53 | 2.75<br>2.77 | 12.73<br>12.69 | 21.48<br>22.00 | | 3 |
| 16 | C₂H₅CON-, C₂H₅CON-, 3,5-diCl-C₆H₃ | 257–260 | 46.94<br>46.79 | 3.66<br>3.58 | 11.73<br>11.65 | 19.80<br>19.76 | | 3 |
| 17 | C₂H₅OCN-, HN-, 3,5-diCl-C₆H₃ | 185–188 | 41.53<br>41.49 | 2.85<br>2.84 | 13.21<br>13.09 | 22.29<br>22.34 | | 2 |
| 18 | C₂H₅OCN-, C₂H₅OCN-, 3,5-diCl-C₆H₃ | 211–213 | 43.09<br>42.98 | 3.36<br>3.42 | 10.77<br>10.75 | 18.17<br>18.19 | | 2 |
| 19 | CH₃NHCN-, HN-, 3,5-diCl-C₆H₃ | 220–222 | 39.62<br>39.49 | 2.66<br>2.59 | 18.49<br>18.47 | 23.39<br>23.45 | | 4 |
| 20 | CH₃NHCN-, CH₃NHCN-, 3,5-diCl-C₆H₃ | 202–205 | 40.02<br>40.14 | 3.08<br>3.07 | 19.45<br>19.42 | 19.69<br>19.71 | | 4 |
| 21 | CH₃N-, CH₃CON-, 3,5-diCl-C₆H₃ | 138–140 | 43.73<br>43.68 | 3.00<br>3.00 | 13.90<br>13.87 | 23.47<br>23.49 | | 3 |
| 22 | CH₃N-, C₂H₅CON-, 3,5-diCl-C₆H₃ | 117–119 | 45.59<br>45.60 | 3.51<br>3.57 | 13.29<br>13.24 | 22.43<br>22.59 | | 3 |
| 23 | CH₃N-, nC₃H₇CON-, 3,5-diCl-C₆H₃ | 85.5–86.5 | 47.29<br>47.26 | 3.97<br>3.95 | 12.73<br>12.69 | 21.48<br>21.53 | | 3 |

Table 1-continued

| Compd. No. | Structure | Melting point(° C) | Elementary assay (%)[2] C | H | N | Cl | S | Ref.[3] Ex. |
|---|---|---|---|---|---|---|---|---|
| 24 | CH₃N, C₂H₅OCON, 3,5-diCl-phenyl | 134–135 | 43.39 / 43.33 | 3.34 / 3.31 | 12.65 / 12.68 | 21.35 / 21.30 | | 2 |
| 25 | CH₃N, CH₃NHCN(O), 3,5-diCl-phenyl | 151–153 | 41.66 / 41.69 | 3.18 / 3.20 | 17.67 / 17.59 | 22.36 / 22.43 | | 4 |
| 26 | CH₃N, CH₃NHCN(S), 3,5-diCl-phenyl | 187–189 | 39.65 / 39.67 | 3.03 / 3.00 | 16.82 / 16.78 | 21.28 / 21.20 | 9.62 / 9.69 | 4 |
| 27 | CH₃N, (CH₃)₂NSO₂N, 3,5-diCl-phenyl | 125–127 | 35.98 / 36.11 | 3.30 / 3.29 | 15.26 / 15.23 | 19.31 / 19.33 | 8.73 / 8.74 | 3 |
| 28 | CH₃N, C₂H₅SCN(S), 3,5-diCl-phenyl | 119–121 | 39.57 / 39.51 | 3.04 / 3.01 | 11.54 / 11.56 | 19.47 / 19.57 | 17.60 / 19.81 | 2 |
| 29 | CH₃CON, C₂H₅OCN(O), 3,5-diCl-phenyl | 163–165 | 43.35 / 43.34 | 3.08 / 3.08 | 11.67 / 11.56 | 19.69 / 19.71 | | 2 |
| 30 | CH₃CON, C₂H₅CON, 3,5-diCl-phenyl | 175–177 | 46.44 / 46.50 | 3.30 / 3.28 | 12.50 / 12.47 | 21.09 / 21.11 | | 3 |
| 31 | C₂H₅OCN, i-C₃H₇NHCN(O), 3,5-diCl-phenyl | 173–175 | 44.68 / 44.70 | 4.00 / 4.02 | 13.90 / 13.86 | 17.59 / 17.62 | | 8 |
| 32 | CH₂=CH–CH₂N, CH₂=CH–CH₂N, 3,5-diCl-phenyl | 82–83 | 51.55 / 51.59 | 4.02 / 4.05 | 12.88 / 12.84 | 21.74 / 21.83 | | 1 |
| 33 | CH≡C–CH₂N, CH≡C–CH₂N, 3,5-diCl-phenyl | 128–129.5 | 52.19 / 52.22 | 2.82 / 2.89 | 13.04 / 13.05 | 22.01 / 22.08 | | 1 |
| 34 | phenyl-N, CH₃-N, 3,5-diCl-phenyl | 101–102.5 | 53.59 / 53.16 | 3.30 / 3.27 | 12.50 / 12.46 | 21.09 / 21.23 | | 9 |

Table 1-continued

| Compd. No. | Structure | Melting point(° C) | Elementary assay (%)[2] | | | | | Ref.[3] Ex. |
|---|---|---|---|---|---|---|---|---|
| | | | C | H | N | Cl | S | |
| 35 | (structure) | 246–248 | 37.42<br>37.35 | 1.92<br>1.86 | 16.03<br>16.00 | 27.05<br>27.03 | 12.23<br>12.16 | 7 |
| 36 | (structure) | 125–127 | 41.39<br>41.18 | 3.13<br>3.10 | 14.48<br>14.51 | 24.43<br>24.38 | 11.05<br>11.06 | 7 |
| 37 | (structure) | >250 | 39.22<br>39.23 | 2.96<br>2.79 | 13.72<br>13.68 | 23.16<br>23.20 | 20.94<br>20.89 | 5 |
| 38 | (structure) | 134–136 | 48.61<br>48.27 | 2.72<br>2.75 | 11.34<br>11.22 | 28.70<br>28.59 | | 9 |
| 39 | (structure) | 116–118 | 54.87<br>55.02 | 3.74<br>3.77 | 12.00<br>11.81 | 20.25<br>20.17 | | 9 |

Note:
[1] Known Compound.
[2] The figures in upper line are calculation and the figures in lower line are found.
[3] The compound was produced by the Reference Example.
[4] Index of Refraction Note: (1) Known Compound.
(2) The figures in upper line are calculation and the figures in lower line are found.
(3) The compound was produced by the Reference Example.
(4) Index of Refraction Among the compounds listed in Table 1, following compounds are found to be preferable as the active ingredient of the fungicide according to this invention:
1-methyl-2-acetyl-4-(3',5'-dichlorophenyl) urazole,
1-methyl-2-ethyl-4-(3',5'-dichlorophenyl) urazole,
1-methyl-2-n-propyl-4-(3',5'-dichlorophenyl) urazole,
1-methyl-2-isopropyl-4-(3',5'-dichlorophenyl) urazole,
1,2-dimethyl-4-(3',5'-dichlorophenyl) urazole and
1-methyl-2-phenyl-4-(3',5'-dichlorophenyl) urazole.

Though 1,2-substituted-4-(3',5'-dichlorophenyl) urazole derivatives may be applied to plants as such as an agricultural fungicide, it is convenient to use the compound diluted with a conventional adjuvant in the form of an emulsion, a wettable powder or a dust conventional adjuvants include a liquid or solid carrier, an emulsifier, a dispersing agent, a spreader, a penetrant and a surface active agent.

Examples of the liquid carriers which may be used according to this invention include a wide variety of solvents; for example, water; alcohols such as methyl alcohol, ethyl alcohol and ethylene glycol; ketones such as acetone, methyl ethyl ketone and cyclohexanone; esters such as methyl ether, dioxane and cellosolve; aliphatic hydrocarbon such as gasoline and kerosene; aromatic hydrocarbons such as benzene, toluene, xylene, solvent naphtha and methyl naphthalene; halogenated hydrocarbons such as dichloromethane, trichlorobenzene and carbon tetrachloride; acid amides such as dimethylformamide; esters such as ethylacetate, butylacetate, glycerides of aliphatic acids; and nitriles such as acetonitrile.

Examples of the solid carriers which may be used according to this invention include, for example, clay, kaolin, bentonite, talc, diatomaceous earth, gypsum, vermiculite, alumina, sulfur, white carbon and carboxymethyl cellulose. Such solid carriers may be used alone or in a mixture of two or more.

Suitable surface active agents may be, for example, of the nonionic type, some as polyoxyethylene alkylaryl ethers and polyoxyethylene sorbitol monoalurates; the cationic type, such as alkyl dimethylbenzyl ammonium chlorides and alkyl pyridinium chlorides; the anionic type, such as alkyl-benzene sulfonates; lignine sulfonates and sulfates of higher alcohols; and the amphoteric type, such as alkyl dimethyl betaines and dodecylaminoethyl glycine.

The aforementioned adjuvants may be used alone or in mixtures of two or more.

The emulsion may be prepared by formulating 10 to 50 parts by weight of the active ingredient compound, 10 to 40 parts of a solvent and 5 to 20 parts of a surface active agent to form a concentrate which is diluted with water to a predetermined concentration and applied to plants or soil by, for example, spraying.

The wettable powder may comprise 10 to 50 parts by weight of the active ingredient compound, 10 to 40 parts of a solid carrier and 5 to 20 parts of a surface active agent. The powder may be used after diluting with water.

The dust may be a uniform mixture of 1 to 5 parts by weight of the active compound and 95 to 99 parts of a solid carrier.

The agricultural fungicides according to this invention may be used together with one or more other active ingredients which do not adversely affect fungicidal activity of the useful compound; such as insecticides, mitecides, and/or other fungicides.

The fungicides according to this invention may be applicable to foliage and soil treatments and the effective dosage thereof is, in general, from 500 to 1500 ppm in case of foliage treatment and from 50 g to 300 g per 100 m² in case of soil treatment.

It has been found that the agricultural fungicide according to this invention possesses a wide fungicidal spectrum for preventing various plant diseases which are observed on fruits, such as apples and grapes; vegetables such as tomatoes and cucumbers; beans and rice plants. Such diseases include rice sheath blight disease, Botrysis gray mold disease, rice brown spot disease, Alternaria leaf spot and Sclerotinia spot. It has also been found that the fungicides are effective against two or more diseases simultaneously and show extremely low toxicity to humans and fish as well as low phytotoxicity.

This invention will be explained in detail by means of the following Examples and Test Examples. However it should be understood that this invention is in no way limited by these Examples in which all parts are by weight unless expressly otherwise stated.

EXAMPLE 1 (DUST)

The following ingredients were mixed and pulverized to obtain a dust:

| | |
|---|---|
| Compound No. 3 | 3 parts |
| A mixture of clay and talc | 97 parts |

EXAMPLE 2 (WETTABLE POWDER)

The following ingredients were mixed and pulverized to form a wettable powder:

| | |
|---|---|
| Compound No. 17 | 20 parts |
| A mixture of clay and diatomaceous earth | 75 parts |
| Sodium alkylbenzene sulfonate | 3 parts |
| Polyoxyethylene nonylphenyl ether | 2 parts |

EXAMPLE 3 (EMULSION)

The following ingredients were mixed under agitation to form an emulsion.

| | |
|---|---|
| Compound No. 34 | 50 parts |
| Xylene | 40 parts |
| Polyoxyethylene nonylphenyl ether | 6 parts |
| Sodium alkylbenzene sulfonate | 4 parts |

TEST EXAMPLE 1

Preventive effect against rice sheath blight disease.

Rice plants (cultivator: Kinmaze), which were at the 5 - 6 leaf stage and were grown in 9 cm pots in a green house and cut at 20 - 30 cm height, were treated with suspensions of wettable powder of the chemicals at various concentrations in an amount of 20 ml per pot by spray application. After air drying, the plants were inoculated with pathogenic mycelia of Pellicularia sasakii which had been cultured on a wheat bran medium for seven days.

These pots were covered with cases made of polyvinyl chloride in order to prevent the escape of humidity and incubation was effected in a chamber maintained at a temperature of from 25° to 27° C. After 20 days, the rating on the disease severity index was determined.

On the other hand, procedures similar to the above were repeated but no chemical was applied to the rice plants. Then, the preventive value of the chemicals was calculated according to the following equation.

Preventive value (%)

$$= \frac{(A) - \text{Disease severity index treated}}{\text{Disease severity index untreated (being A)}} \times 100$$

The results are given in Table 2.

Table 2

| Compound No. | Preventive value (%) | | |
|---|---|---|---|
| | 1000 ppm | 500 ppm | 250 ppm |
| 3 | 100 | 97.4 | 86.3 |
| 4 | 93.2 | 81.4 | 70.8 |
| 5 | 79.6 | 74.3 | 68.5 |
| 6 | 92.0 | 80.5 | 75.5 |
| 9 | 76.3 | 78.0 | 64.8 |
| 10 | 91.4 | 89.6 | 85.3 |
| 14 | 85.4 | 79.6 | 73.1 |
| 15 | 79.6 | 72.9 | 60.4 |
| 16 | 82.4 | 79.3 | 70.4 |
| 17 | 97.5 | 89.7 | 83.4 |
| 19 | 73.2 | 64.8 | 60.3 |
| 20 | 78.9 | 81.6 | 70.4 |
| 21 | 98.4 | 92.2 | 84.6 |
| 22 | 99.3 | 92.0 | 82.1 |
| 26 | 98.4 | 95.7 | 84.2 |
| 27 | 86.3 | 85.2 | 71.4 |
| 28 | 83.5 | 72.4 | 63.5 |
| 29 | 92.6 | 81.8 | 73.2 |
| 30 | 83.2 | 72.4 | 68.8 |
| 32 | 93.4 | 81.6 | 73.2 |
| 33 | 85.6 | 69.7 | 72.4 |
| 34 | 99.3 | 93.2 | 85.5 |
| 35 | 91.4 | 88.0 | 82.1 |
| 36 | 82.6 | 79.4 | |

TEST EXAMPLE 2

Preventive effect against cucumber gray mold disease.

Cotyledons which were cut from cucumber seedlings (cultivator: Sagamihanziro) were dipped in aqueous suspensions of wettable powder having various concentrations of the chemicals and air dried. Pathogenic mycelia of Botrytis cinerea were inoculated onto the cotyledons and incubated in a humidity chamber maintained at 25° C. After 7 days, the rating on the disease severity index was determined.

On the other hand, procedures similar to the above were repeated but no chemical was applied to cotyledons and the preventive value was calculated according to the above equation. The results are given in Table 3.

Table 3

| Compound No. | Preventive value (%) | | |
|---|---|---|---|
| | 1000 ppm | 500 ppm | 250 ppm |
| 2 | 96.5 | 93.2 | 91.8 |
| 3 | 100 | 98.2 | 95.4 |
| 7 | 96.2 | 95.4 | 90.6 |
| 8 | 98.4 | 91.5 | 82.3 |
| 11 | 100 | 98.6 | 92.0 |
| 12 | 83.2 | 72.3 | 69.8 |

Table 3-continued

| Compound No. | Preventive value (%) | | |
|---|---|---|---|
| | 1000 ppm | 500 ppm | 250 ppm |
| 13 | 97.3 | 90.4 | 83.4 |
| 18 | 100 | 98.6 | 95.3 |
| 23 | 97.4 | 82.6 | 80.4 |
| 24 | 83.2 | 76.4 | 63.5 |
| 25 | 100 | 96.3 | 91.5 |
| 31 | 85.4 | 73.2 | 65.4 |
| 37 | 100 | 92.4 | 86.3 |

TEST EXAMPLE 3

Preventive effect against rice brown spot disease.

Rice plants (cultivator: Kinmaze), which were at the 4 - 5 leaf stage and grown in 9 cm pots in a green house, were treated with suspensions of various wettable powders made from the chemicals being tested at predetermined concentrations by means of spraying at a dosage rate of 20 ml per pot and air dried.

Then, a suspension containing pathogenic spores of Cochliobolus miyabeanus was inoculated on the plants and incubated in a humidity chamber at 25° - 27° C. After 48 hours, the number of lesions was counted.

On the other hand, similar procedures were repeated but no chemical was applied. The preventive value was calculated according to the following $$\text{Preventive value (\%)} = \frac{(A) - \text{number of lesions treated}}{\text{Number of lesions untreated (being } A\text{)}} \times 100$$

The results are given in Table 4.

Table 4

| Compound No. | Preventive value (%) | | | |
|---|---|---|---|---|
| | 500 ppm | 250 ppm | 125 ppm | 62.5 ppm |
| 3 | 100 | 99.1 | 92.6 | 86.7 |
| 8 | 97.4 | 92.6 | 81.9 | 72.4 |
| 13 | 100 | 98.0 | 95.2 | 89.4 |
| Control[1] | 98.6 | 91.3 | 72.5 | 63.2 |

Note:
[1]Control chemical was N-3, 5-dichlorosuccinimide

What is claimed is:

1. A compound represented by the formula

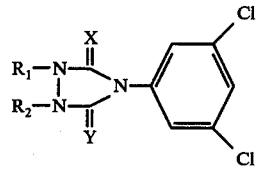

wherein each of X and Y represents oxygen or sulfur; $R_1$ and $R_2$ may be the same or different and represent alkyl having 1 to 4 carbon atoms; allyl; phenyl which may have a substituent selected from the group consisting of halogen or methyl; alkylcarbonyl having 2 to 4 carbon atoms; alkylcarbamoyl having 2 to 4 carbon atoms; ethoxycarbonyl; methylthiocarbamoyl; and (ethylthio) thiocarbamoyl.

2. A compound represented by the formula

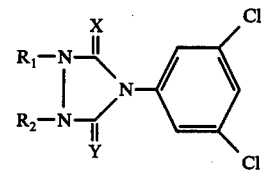

wherein X is oxygen, Y is oxygen or sulfur, $R_1$ is methyl, and $R_2$ is selected from the group consisting of methyl, ethyl, phenyl or acetyl.

3. The compound of 1,2-dimethyl-4-(3',5'-dichlorophenyl) urazole.

4. The compound of 1-methyl-2-phenyl-4-(3',5'-dichlorophenyl) urazole.

5. A composition which comprises a fungicidal amount of the compound represented by the formula

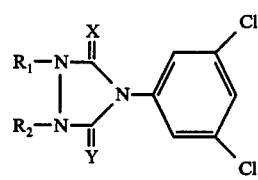

wherein X and Y represent oxygen or sulfur, $R_1$ and $R_2$ may be the same or different and represent alkyl having 1 to 4 carbon atoms; allyl; phenyl which may have a substituent selected from the group consisting of halogen or methyl; alkylcarbonyl having 2 to 4 carbon atoms, alkylcarbamoyl having 2 to 4 carbon atoms, ethoxycarbonyl, methylthiocarbamoyl, or (ethylthio) thiocarbamoyl, and an adjuvant.

6. The composition according to claim 5 wherein X represents oxygen, Y represents oxygen or sulfur and $R_1$ represents methyl and $R_2$ represents methyl, ethyl, phenyl or acetyl.

7. A method of killing fungi which comprises applying to said fungi an effective amount of a compound according to claim 1.

8. A method of killing fungi according to claim 7 wherein X represents oxygen, Y represents oxygen or sulfur, $R_1$ represents methyl and $R_2$ represents methyl, ethyl, or acetyl.

9. The method according to claim 7 wherein said compound is 1,2-dimethyl-4-(3',5'-dichlorophenyl) urazole.

10. The method according to claim 7 wherein said compound is 1-methyl-2-phenyl-4-(3',5'-dichlorophenyl) urazole.

* * * * *